United States Patent
Tani et al.

(10) Patent No.: US 6,668,624 B2
(45) Date of Patent: Dec. 30, 2003

(54) METHOD AND APPARATUS FOR ANALYZING ORGANIC MACROMOLECULAR COMPONENT AND APPLICATION THEREOF

(75) Inventors: Michiko Tani, Ohmiya (JP); Yutaka Hayashibe, Ohmiya (JP); Masaaki Kato, Ohmiya (JP); Minoru Takeya, Ohmiya (JP)

(73) Assignee: Mitsubishi Materials Corporation, Tokyo (JP)

( * ) Notice: Subject to any disclaimer, the term of this patent is extended or adjusted under 35 U.S.C. 154(b) by 122 days.

(21) Appl. No.: 09/820,794

(22) Filed: Mar. 30, 2001

(65) Prior Publication Data

US 2002/0134142 A1 Sep. 26, 2002

Related U.S. Application Data

(63) Continuation of application No. 09/796,468, filed on Mar. 2, 2001.

(30) Foreign Application Priority Data

Mar. 3, 2000 (JP) .......................................... 2000-059219
Jan. 29, 2001 (JP) .......................................... 2001-019767

(51) Int. Cl.[7] ............................................. G01N 30/06
(52) U.S. Cl. ..................... 73/61.52; 73/61.55; 73/61.56; 73/61.58; 422/68.1; 422/70; 436/86; 436/161; 436/178
(58) Field of Search ........................ 73/61.52, 61.53, 73/61.55, 61.56, 61.58; 422/68.1, 70, 80; 436/86, 161, 177, 178

(56) References Cited

U.S. PATENT DOCUMENTS

| 3,615,224 | A | * | 10/1971 | Stern et al. ............... 73/61.52 |
| 3,856,471 | A | * | 12/1974 | Winitz et al. ............... 422/70 |
| 5,843,788 | A | * | 12/1998 | Rexroad, Jr. et al. ....... 436/161 |
| 6,260,407 | B1 | * | 7/2001 | Petro et al. ............... 73/61.52 |
| 6,498,040 | B1 | * | 12/2002 | Yokoyama et al. ........ 73/61.55 |

FOREIGN PATENT DOCUMENTS

| JP | 2000-171451 | * | 6/2000 | ................ 73/61.55 |
| JP | 2000-171452 | * | 6/2000 | ................ 73/61.55 |

* cited by examiner

*Primary Examiner*—Daniel S. Larkin
(74) *Attorney, Agent, or Firm*—Oblon, Spivak, McClelland, Maier & Neustadt, P.C.

(57) ABSTRACT

A method and an apparatus for efficiently analyzing an organic macromolecular component contained in a sample with high precision are provided. The method and the apparatus for analyzing the organic macromolecular component are based on a flow analysis method with a measuring system including a sample introduction section, a preparation section, and a measuring section, and include the steps of supplying a sample together with a carrier solution into the measurement system through the introduction section, leading the sample to the preparation section and separating an organic macromolecular component from the sample, and leading the separated organic macromolecular component to the measuring section for analysis. Herein, the step of separating the organic macromolecular component includes the steps of the organic macromolecular component in the sample being adsorbed on a resin, and introducing an eluant solution into the preparation section and eluting the organic macromolecular component adsorbed on the resin.

24 Claims, 6 Drawing Sheets

METHOD AND APPARATUS FOR ANALYZING ORGANIC MACROMOLECULAR COMPONENT AND APPLICATION THEREOF

BACKGROUND OF THE INVENTION

1. Field of the Invention

The present invention relates to a method and an apparatus for analyzing organic macromolecular components in a solution based on a flow analysis method, and relates to applications thereof. In particular, the present invention relates to an analytical method and an apparatus suitable for quantitatively analyzing very small amounts of glues or gelatins contained in metallic electrolytic solutions such as copper electrolytic solutions and plating solutions.

2. Discussion of the Background

Additives are added to electrolytic solutions and plating solutions for various purposes, such as improving brightness and smoothness of electrodeposited metal surfaces, hardening plated layers, etc. Generally, glue additives are used in electrolytic smelting, and gelatins are used in plating. Herein, for quality control, it is very important to keep concentrations thereof within specified ranges. For example, although glues are used for improving the smoothness of electrodeposited surfaces, when concentrations thereof are too high polarization is increased to such a great degree that there are problems with deposition of impurities such as bismuth contained in the electrolytic solutions, etc.

Therefore, a method for analyzing proteins, such as glues or gelatins contained in solutions, with a high degree of precision has been required. Most of the conventional methods for analyzing proteins are performed under conditions being from weakly acidic to weakly basic, and there are few analytical methods which can be applied under strongly acidic conditions of a pH 1 or less, as in electrolytic solutions, plating solutions, etc. Hitherto, proteins such as glues or gelatins contained in electrolytic solutions, plating solutions, etc., have been measured by a potentiometric titration, the Kjeldahl method, etc., although specific apparatuses and complicated operations have been required in those cases. In the Kjeldahl method, glues are measured after the nitrogen in the glues is converted into ammonia, although in many cases nitrogen compounds other than proteins are contained in the electrolytic solutions so as to make precise measurements difficult.

In addition, as a quantitative method for analyzing gelatins and glues in a strongly acidic solution, a method in which gelatins and glues are collected on membrane filters, are bonded with a specific reagent (Amide Black 10B coloring matter), and after excess coloring, matters are washed out, the coloring matters are eluted so as to determine gelatins, etc., (Japanese Unexamined Patent Application Publication No. 2-69660); and a method in which after gelatins, etc., are collected on a filter, the resulting filter is dried so as to determine gelatins, etc., based on reflectance (Japanese Unexamined Patent Application Publication No. 6-337247), etc., are reported. Regarding these methods, there are, however, problems in that the amount of collected glues is greatly affected by pore diameters of the filter so as to increase measurement errors. A filtering apparatus for collecting with a filter and complicated operations therefor are required, and the analytical cost is increased due to the disposable filters.

SUMMARY OF THE INVENTION

The present invention has solved the aforementioned problems in the conventional analytical methods. Accordingly, the present invention provides a flow analysis method and an apparatus by which organic macromolecular components such as glues and gelatins in solutions can be promptly and precisely quantified even in strongly acidic solutions.

The present invention resides in the completion of a measurement system with a high degree of reliability and with handling ease, in which the operations of separating an organic macromolecular component in a solution by adsorption on a resin, leading this to a gel permeation chromatograph, and analysis are performed based on the flow analysis.

That is, the present invention relates to the following flow analysis methods for separating and analyzing an organic macromolecular component in a sample.

According to a first aspect of the present invention, a method for analyzing an organic macromolecular component based on a flow analysis method with a measurement system including a sample introduction section, a preparation section, and a measuring section, includes the steps of supplying a sample together with a carrier solution into the measurement system through the introduction section, leading the sample to the preparation section and separating the organic macromolecular component in the sample, and leading the separated organic macromolecular component to the measuring section for analysis. Herein, the step of separating the organic macromolecular component includes the steps of adsorbing the organic macromolecular component in the sample on a resin and introducing an eluant solution into the preparation section and eluting the organic macromolecular component adsorbed on the resin.

Preferably, the method of analysis may further include the steps of supplying the sample into the measurement system through the introduction section while a pipeline for feeding the sample running from the introduction section to the preparation section and a pipeline for discharging the solution running from the preparation section to the outside of the measurement system are connected to the preparation section; and leading the sample to the preparation section, where the organic macromolecular component in the sample is adsorbed on the resin in the preparation section, and leading the discharged solution from the preparation section to the outside of the measurement system. Switchable pipelines are connected to the preparation section so that a pipeline for supplying the eluant solution and a pipeline connected to the measuring section are connected to the preparation section, introducing the eluant solution into the preparation section so as to elute the organic macromolecular component adsorbed on the resin, and leading the resulting solution containing the organic macromolecular component to the measuring section for analysis.

Preferably, the method of analysis may further include the steps in which the eluant solution is used after a buffer solution to prevent the organic macromolecular components from coagulating is added thereto, or the buffer solution is added to the solution containing the organic macromolecular component between the preparation section and the measuring section.

Preferably, the method of analysis may further include the step in which a gel permeation chromatography is used as an analyzing device so as to fractionate and analyze the organic macromolecular component separated from the sample.

Preferably, the method of analysis may further include the step in which an amount of glues or gelatins is separated from the sample, or amounts of decomposition products thereof are measured.

Preferably, the method of analysis may further include the step in which a gel permeation chromatography is used as an analyzing device in the measuring section so as to fractionate glues or gelatins separated from the sample and to measure the amount thereof or the amounts of decomposition products thereof.

Preferably, the method of analysis may further include the step in which an acid-proof and hydrophobic adsorption resin is used as a resin for adsorbing the organic macromolecular component in the sample.

Preferably, the method of analysis may further include the step in which an electrolytic solution taken from a step of metallic electrolysis or a plating solution taken from a step of plating is used as a sample solution.

Preferably, the method for controlling a metallic electrolysis process with the method of analysis may further include the steps of taking a sample solution from an electrolytic solution in the step of metallic electrolysis, measuring the amount of glues or gelatins separated from the sample of the electrolytic solution or amounts of decomposition products thereof, and feeding the results of the measurement back to the step of metallic electrolysis.

Preferably, the method for controlling a plating process with the method of analysis may further include the steps of taking a sample solution from a plating solution in the step of plating, measuring the amount of glues or gelatins separated from the sample of the plating solution or amounts of decomposition products thereof, and feeding the results of the measurement back to the step of plating.

In the method of analysis according to the present invention, as described above, a series of the operations of separating proteins and organic macromolecular components such as glues and gelatins contained in the sample by adsorption on the resin from the sample, are lead to a gel permeation chromatograph, where analysis is performed based on the flow analysis method. Since the operations from the introduction of the sample to the analysis of the organic macromolecular component can be continuously performed in a short time, the analytical results can be promptly obtained. Therefore, regarding the organic macromolecular component, behaviors during decomposition and intermediate products can be grasped. Since the separation is performed using the hydrophobic adsorption resin and the analysis is performed using the gel permeation chromatography, the organic macromolecular component can be analyzed independent of the molecular weight. Furthermore, when the organic macromolecular components are fed to the measuring section, a buffer solution for preventing the coagulation thereof may be added so as not to cause a blockage of the pipeline, etc. Therefore, the analysis can be performed with a high degree of reliability. This buffer solution may be blended beforehand with the eluant solution or may be added between the preparation section and the measuring section. When the buffer solution is added after the organic macromolecular components adsorbed on the resin are eluted, the effect of eluting is improved and the effect of preventing the organic macromolecular components from coagulating is also improved.

The flow analysis method according to the present invention can be applied to strongly acidic solutions such as metallic electrolytic solutions and plating solutions by using an acid-proof and hydrophobic adsorption resin as the resin for adsorbing the organic macromolecular components. Therefore, the quantitative analysis of glues contained in the electrolytic solutions of copper electrolytic smelting, etc., can be easily performed so that it can be used as a method for controlling electrolytic operations according to the method of analysis of the present invention. Since a continuous automatic analysis is possible instead of a conventional batch method for controlling electrolysis by manual work, long term and accurate operation control of the electrolytic smelting is possible.

The present invention further relates to the following apparatuses for flow analysis.

According to a second aspect of the present invention, an apparatus for flow analysis of an organic macromolecular component includes a sample introduction section, a preparation section, and a measuring section integrally connected by pipelines, in which the preparation section is provided with an adsorbing device for adsorbing the organic macromolecular component and an eluting device for separating the organic macromolecular component in the sample, and the measuring section is provided with a fractionating and analyzing device for fractionating and analyzing the separated organic macromolecular component.

Preferably, the apparatus for flow analysis may further include a column filled with a resin for adsorbing the organic macromolecular component in the sample, and a pipeline for introduction, running from the introduction section to the outside of the measurement system, and a pipeline for elution, running from a supply source of the elution solution to the measuring section, where each is connected to the column so as to be freely switched from each other, the adsorbing device and the eluting device for the organic macromolecular component being composed thereof.

Preferably, the apparatus for flow analysis may further include an acid-proof and hydrophobic adsorption resin which is used as a resin for adsorbing the organic macromolecular component in the sample, and the protein is separated using a column filled with the aforementioned resin.

Preferably, the apparatus for flow analysis may further include a buffering section which is between the preparation section and the measuring section so as to add a buffer solution for preventing the organic macromolecular components from coagulating.

Preferably, the apparatus for flow analysis may further include a gel permeation chromatograph in the measuring section as an analytical device for measuring the organic macromolecular component.

Preferably, the apparatus for flow analysis may further include a column filled with a hydrophilic polymer gel having an exclusion molecular weight limit of $5 \times 10^3$ or more in the gel permeation chromatograph so that the molecular weight fractionation of the proteins is performed using the hydrophilic polymer gel.

Preferably, the apparatus for flow analysis may further include columns in a plurality of stages, each column being filled with a hydrophilic polymer gel having a different exclusion molecular weight limit.

Preferably, the apparatus for flow analysis may further include a thermostatic chamber in the measuring section, and may be further provided with a gel permeation chromatograph in the thermostatic chamber.

Preferably, the apparatus for flow analysis may further include sulfuric acid, hydrochloric acid, or nitric acid each having a concentration of 0.1 M or less, or a mixed acid solution thereof which is used as a carrier solution.

Preferably, the apparatus for flow analysis may further include 20% to 40% of methanol, ethanol, other lower alcohols, or 20% to 40% of acetonitrile which is used as the eluant solution.

Preferably, the apparatus for flow analysis may further include a mixture solution of the eluant solution and a phosphoric acid buffer solution for preventing organic macromolecular components from coagulating, which is introduced into a detecting device in the measuring section.

Preferably, the apparatus for flow analysis may further include a flow rate of the phosphoric acid solution which is introduced into the detecting device in the measuring section as 1 mL/min or less.

Preferably, the apparatus for flow analysis may further include pipelines which are made of tubes 1 mm or less in inner diameter, and made of stainless steel, TEFZEL (i.e., ethylene-tetrafluoroethylene), or PEEK.

Preferably, the apparatus for flow analysis may further include an automatic control device for controlling the feed of the solution and the discharge of the solution in the sample introduction section and in the preparation section, for temperature adjustment in the measuring section, and for the actions of a detecting section so as to continuously and automatically perform operations from sample introduction to fractionation, and analysis by way of separation of the organic macromolecular component.

According to the aforementioned apparatus for flow analysis, the organic macromolecular components contained in the sample can be separated with operational ease and can be analyzed. Furthermore, the column for adsorbing the organic macromolecular components, and the pipelines for sample introduction and for leading the separated organic macromolecular component to the measuring section, each connected to the resin column so as to be freely switched from each other, are provided. Therefore, feed of the sample to the resin column and discharge, adsorption of the organic macromolecular component by the resin and elution, and feed of the solution to the measuring section can be mechanically and smoothly performed in a short time. By the buffering section being provided between the preparation section and the measuring section, separated organic macromolecular components are prevented from coagulating so as not to cause a blockage of the pipeline and the analysis can be performed with a high degree of reliability.

Furthermore, since a measurement system is made so that the acid-proof and hydrophobic adsorption resin is used as the resin for adsorbing the organic macromolecular component in the sample, the gel permeation chromatography is used as the analytical device in the measuring section, the column filled with the hydrophilic polymer gel having the exclusion molecular weight limit of $5 \times 10^3$ or more is preferably used for the gel permeation chromatography, and if necessary, columns are connected in a plurality of stages, each column being filled with a hydrophilic polymer gel having a different exclusion molecular weight limit, precise analysis can be performed in response to the molecular weight of the organic macromolecular component. The aforementioned columns are preferably provided in a thermostatic chamber.

Since sulfuric acid, hydrochloric acid, or nitric acid each having a concentration of 0.1 M or less, or a mixed acid solution thereof is used as a carrier solution, 40% or less of methanol, ethanol, other lower alcohols, or 40% or less of acetonitrile is used as the eluant solution, and preferably, a mixture solution of the eluant solution and a phosphoric acid buffer solution for preventing organic macromolecular components from coagulating is used, the proteins can be precisely and smoothly analyzed.

In the apparatus for analysis according to the present invention, since the measurement system of the sample introduction section to the measuring section by way of the preparation section is integrally communicated by pipelines, and pipelines connected to the preparation section are made so as to be freely switched from each other, the operations of feeding the solution and discharging the solution in each section are able to be automatically controlled. Therefore, a series of operations from the introduction of the sample to the analysis can be automated with the aforementioned automatic control device being provided.

DESCRIPTION OF THE PREFERRED EMBODIMENTS

Figure 1:
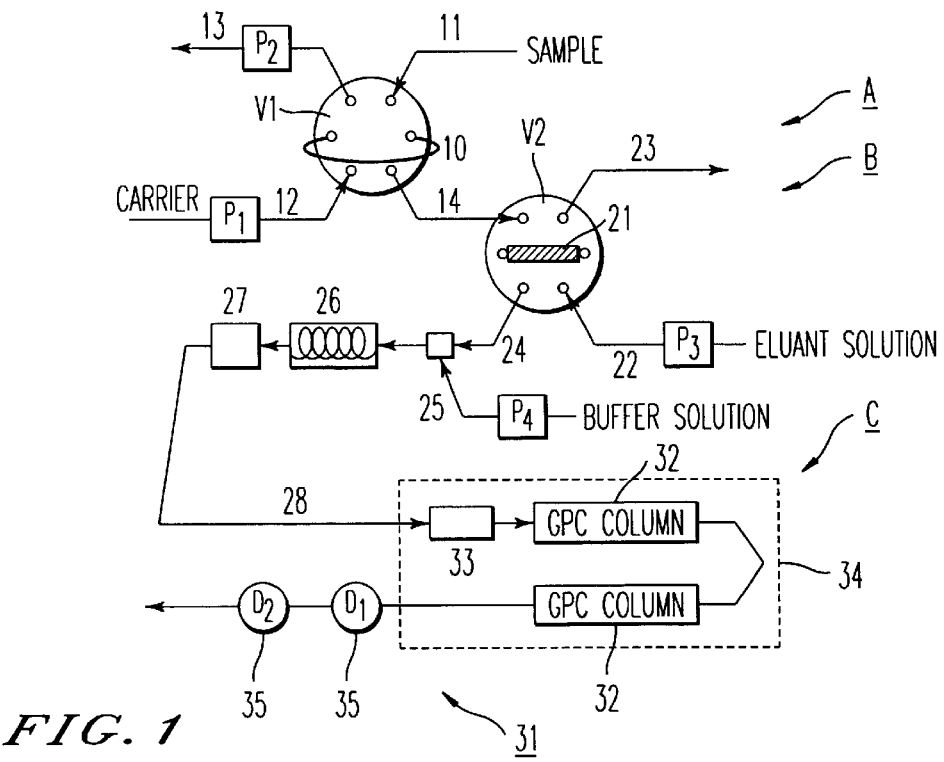
FIG. 1 is a conceptual diagram of an analysis apparatus (system) according to the present invention.
Figure 2:
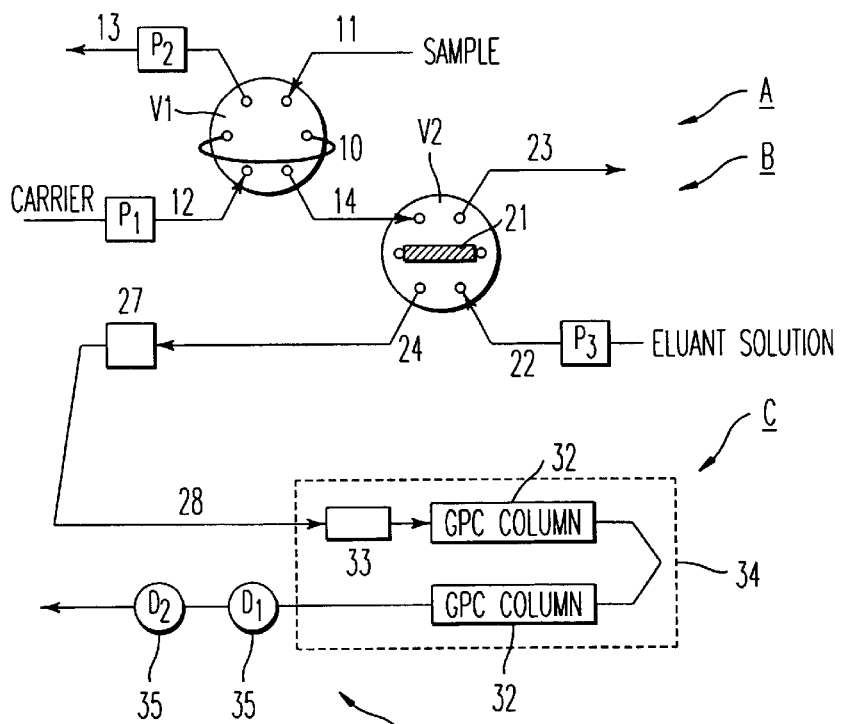
FIG. 2 is a conceptual diagram of a simplified configuration according to an embodiment of the analytical; system shown in FIG. 1.

The present invention will be specifically explained using the following embodiments with reference to the drawings showing a method of analysis and an apparatus according to the present invention. FIGS. 1 and 2 are conceptual diagrams showing the configurations of analytical systems according to the embodiments of the present invention. In the analytical system according to the present invention as shown in the drawings, a sample solution introduction section A, a sample preparation section B, and a measuring section C are sequentially and integrally communicated by pipelines. In the sample preparation section B, a resin-filled column 21 for adsorbing organic macromolecular components in the sample solution and a pipeline 22 for an eluant solution connected to the column 21 are provided. In the measuring section C, columns 32 of a gel permeation chromatograph 31 connected to the column 21 and detecting devices 35 thereof are provided.

In the analytical system as shown in FIG. 1, a pipeline 25 for a buffer solution and a mixing section 26 are further provided between the column 21 in the sample preparation section B and the measuring section C. The columns 32 with different gel mesh diameters for the gel permeation chromatograph 31 in the measuring section C are provided in a plurality of stages in a thermostatic chamber 34. The analytical system as shown in FIG. 2 has a simplified configuration in which the pipeline 25 for the buffer solution and the mixing section 26 are omitted from the configuration as shown in FIG. 1.

The sample solution introduced in the measurement system is led to the aforementioned column 21, and the organic macromolecular components in the sample solution are adsorbed and separated. Then the pipelines are switched so as to feed the eluant solution into the column 21 and the organic macromolecular components are eluted. Thereafter, the resulting solution containing the organic macromolecular components is led to the columns 32 of the gel permeation chromatograph 31 and the detecting devices 35 thereof so as to be fractionated and analyzed.

Each constituent of the aforementioned analytical system will be explained below.

(A) Sample Introduction Section

The introduction section A for the sample solution includes an introducing device for the sample solution and a feeding device for a carrier solution transferring the sample solution to the measurement system. As the feeding device for the carrier solution, a solution feed pump $P_1$ can be used. As the solution feed pump $P_1$, a plunger pump with a reduced pulsating flow is suitable. Dilute sulfuric acid as the carrier solution is fed to the measurement system through a pipeline 12 by the solution feed pump $P_1$. Dilute sulfuric acid and water may be separately introduced in the system using, for example, a double-plunger pump provided with a solution feed pump for supplying water and a solution feed pump for supplying dilute sulfuric acid as the solution feeding device $P_1$. As the carrier solution, for example, sulfuric acid, hydrochloric acid, or nitric acid each having a concentration of 0.1 M or less, or a mixed acid solution thereof can be used.

As the introducing device for the sample solution, a valve device (six-way valve) $V_1$ provided with a loop 10 for holding a specified amount of sample solution is used. This valve device $V_1$ is provided with six connection holes. The loop 10 for holding a specified amount of sample solution is provided between a pair of the connection holes on opposite sides, and each of the other connection holes is made so as to communicate with a pipeline 11 for supplying the sample solution, a pipeline 12 for introducing the carrier solution, a pipeline 13 for discharging the solution, or a pipeline 14 far transferring to the measuring section C. In the pipeline 13 for discharging the solution, a solution feed pump $P_2$ is provided.

The sample solution is suctioned by the solution feed pump $P_2$, and is introduced into the aforementioned loop 10 through the pipeline 11 for supplying the sample solution so that a specified amount of the sample solution is held. The amount of the sample solution can be controlled by the length of the loop 10. During the measurement, the loop 10 is connected to the pipeline 12 for introducing the carrier solution, and the pipeline 14 for the measurement system, respectively, according to the position of the valve device $V_1$ so that a specified amount of the sample solution is fed to the sample preparation section B by the carrier solution. After the sample solution is fed, the pipelines are switched by turning the valve device $V_1$, and the loop 10 is connected to the pipeline 11 for supplying the sample solution, and the pipeline 13 for discharging the solution so that the remaining solution in the loop is discharged and new sample solution is introduced into the loop 10. A plurality of sample solution tanks, although not shown in the drawings, may be connected to the pipeline 11 for supplying the sample solution, with a switching device for pipelines, although not shown in the drawings, therebetween so as to appropriately select the sample solution to be introduced in the measurement system from a plurality of sample solutions.

(B) Sample Preparation Section

The sample preparation section B is provided with the resin-filled column 21 and the pipeline 22 for the eluant solution, which is connected to the column 21. In the analytical system as shown in the drawings, a valve device $V_2$ having six connection holes is provided similarly to the valve device $V_1$ in the sample introduction section, and the aforementioned column 21 is provided between a pair of the connection holes on opposite sides of the valve device $V_2$. Each of the other connection holes is made so as to communicate with a pipeline 14 for connecting to the introduction section A, the pipeline 22 for the eluant solution, a pipeline 23 for discharging the solution, or a pipeline 24 for the measurement system transferring to the measuring section C.

The aforementioned column 21 is filled with the resin for adsorbing organic macromolecular components contained in the sample solution. Specifically, for example, when the sample solution is a metallic electrolytic solution or a plating solution, a hydrophobic adsorbing resin for adsorbing proteins such as glues and gelatins contained in the solution is applied as the filler. This resin, an acid-proof hydrophobic adsorbing resin is suitable so as to tolerate strongly acidic solutions such as a metallic electrolytic solution and a plating solution. Styrene-divinylbenzene-based nonpolar resins, ester-based resins of intermediate polarity, etc., are used as the preferable resins. The nonpolar resins and resins of intermediate polarity have superior performance for adsorbing very small amounts of proteins in the solution compared to ion exchange resins. The styrene-divinylbenzene-based resins have a high durability against acids. The proteins contained in the sample solution are adsorbed and are separated from the sample solution by these resins.

The proteins adsorbed on the resin are eluted from the resin by the eluant solution. The eluant solution is fed to the resin-filled column 21 through the pipeline 22. A solution feed pump $P_3$ is provided in the pipeline 22 for the eluant solution. After the channel of the aforementioned column 21 is switched according to the position of the valve device $V_2$ so as to communicate with the pipeline 22 for the eluant solution arid the pipeline 24 for the measurement system, the eluant solution is introduced into the column 21. As the eluant solution, aqueous solutions at organic solvents can be used. Specifically, aqueous solutions of lower alcohols such as methanol and ethanol, acetonitrile, etc., can be used. Among these, acetonitrile has superior effects for eluting. The concentration of acetonitrile is preferably 20 to 50% by weight, and more preferably, is 20 to 40% by weight. When the concentration is too low, the elution of proteins is insufficient. On the other hand, when the concentration is too high, proteins precipitate so as to hinder the feed of the solution and the measurement.

A specified amount of the sample solution is introduced in the column 21 from the introduction section A through the pipeline 14. The organic macromolecular components in the solution are adsorbed on the resin, and the filtrate passed through the column is discharged to the outside of the system through the pipeline 23 for discharging the solution. After completion of the adsorption, pipelines are switched according to the position of the valve device $V_2$ so that the column 21 is connected to the pipeline 22 for the eluant solution and pipeline 24 for the measurement system. Then, the eluant solution is introduced into the column. The organic macromolecular components adsorbed on the resin are eluted into the solution by the eluant solution, and are fed to the measuring section C through the pipeline 24. Regarding the low concentration of proteins, etc., the concentration of the proteins can be increased by repeating the adsorption with the resin.

Before the introduction of the sample solution and the eluant solution into the resin-filled column 21, if necessary, preparation of the inside of the column is preferably performed. For example, dilute sulfuric acid solution is passed beforehand through the column, and the inside of the column is preferably replaced by the carrier solution so as to prevent metals from depositing and to accelerate the adsorption of the proteins. When the concentration of acids in the column is high, washing with water is preferably performed beforehand.

In the analytical system as shown in FIG. 1, the pipeline 25 for introducing the buffer solution, a solution feed pump $P_4$ therefor, and the mixing section 26 are provided between the sample preparation section B and the measuring section C. The buffer solution prevents eluted proteins (organic macromolecular components) such as glues and gelatins from coagulating. Neutral or weakly acidic solutions such as phosphoric acid are used as the buffer solution. The buffer solution is introduced into the pipeline 24 for the measurement system by the solution feed pump $P_4$, then is added to the eluant solution containing the organic macromolecular components, and the resulting solution is uniformly mixed by passing through the mixing section 26. The mixing section 26 is made of the coiled part of the pipeline 24 so as to increase the length of the pipeline, and thereby, the mixing time is ensured. A degasser 27 is provided at the outlet of the mixing section 26 for degassing. The eluant solution containing the organic macromolecular components, mixed with the buffer solution, is introduced into the measuring section C through a pipeline 28 for the measurement system after passing through the mixing section 26.

As shown in FIG. 2, by using a solution prepared beforehand by mixing the buffer solution and the eluant solution, the pipeline 25 for introducing the buffer solution and the mixing section 26, may be omitted so as to simplify the measurement system. When the eluting effect is decreased by using the aforementioned mixed solution, the pipeline 25 for introducing the buffer solution may be provided after the step of elution, as shown in FIG. 1, so that the eluant solution and the buffer solution are preferably introduced separately. In the case in which phosphoric acid is used as the buffer solution, the flow rate of phosphoric acid introduced into the measurement system is preferably about 1 mL/min or less.

(C) Measuring Section

The measuring section C is provided with the gel permeation chromatograph (GPC) 31 as the measuring device. The gel permeation chromatograph 31 includes the GPC columns 32 and the detecting devices 35. Regarding the GPC columns 32, a plurality of columns each filled with a different gel mesh diameter are provided in a plurality of stages so as to fractionate and analyze proteins (organic macromolecular components) having a wide distribution of molecular weights. In order to reduce the error due to the change in temperature, these gel-filled columns are provided in the thermostatic chamber 34. Specifically, for example, a column filled with a hydrophilic polymer gel having an exclusion molecular weight limit of 5,000 or more, 10,000 or more, or $2 \times 10^5$ to over $2 \times 10^6$ is used. If necessary, columns, each filled with a hydrophilic polymer gel having a different exclusion molecular weight limit, are provided in a plurality of stages. In order to protect the GPC columns 32, a guard column 33 is provided before the GPC columns 32.

The organic macromolecular components, such as proteins introduced into the GPC columns 32, are diffused along the direction of the flow in accordance with the mesh diameters (exclusion molecular weight limit) of the gels in response to the molecular weights by passing through the columns. Specifically, for example, proteins having molecular weights of 5,000 or less or of 10,000 or less are fractionated and diffused in the first stage column 32, and proteins having molecular weights of 5,000 or more or of 10,000 or more are fractionated and diffused in the second stage column 32. In another case, the first stage column 32 is filled with a polymer gel having an exclusion molecular weight limit of $2 \times 10^5$ and the second stage column 32 is filled with a polymer gel having an exclusion molecular weight limit of $2 \times 10^6$, so that the proteins are fractionated and diffused in accordance with the exclusion molecular height limit of each column. The resulting solution in which organic macromolecular components such as proteins are diffused, is led to the detecting devices 35 so as to be quantitated.

As the detecting device 35, a method of direct and optical quantitation of proteins, etc., can be used. The measuring section C nay be provided with a pipeline for introducing a coloring agent and a mixing section, so as to quantitate based on the strength of coloring, etc.

The analytical system according to the present invention preferably includes an automatic control device. That is, the automatic control device may be provided, in which each part of the operation, for example, each solution feed pump and each valve device, provided in the sample solution introduction section and the preparation section, temperature adjustment of the measuring section, and actions of the detection section are controlled, and a series of operations from introducing the sample solution, to fractionating and analyzing the organic macromolecular components such as proteins, are continuously and automatically performed. According to the aforementioned automatic analytical system, glues in the electrolytic solution, etc., can be determined in real time.

The present invention has the advantages as follows:

(a) According to the flow analysis system (method or apparatus) of the present invention, the quantitative analysis of proteins, etc., which has been hitherto individually and manually performed, can be mechanically and promptly performed in a short time with no measurement error, due to manual work, and with high measurement precision. Furthermore, the analytical time can be decreased by a large degree. In particular, since proteins, etc., can be fractionated and analyzed in response to the molecular weight, behaviors during decomposition and the amounts of intermediate products, etc., of glues, etc., contained in the sample solution can be grasped. In addition, since proteins can be analyzed after being concentrated by repeating the adsorption on the resin, low concentrations of proteins, etc., can be fractionated and analyzed. As described above, the analytical system according to the present invention can be used as a method for process control of an electrolytic operation.

(b) The apparatus for analysis according to the present invention is suitable for automation since the analysis is based on the flow analysis in which separation of proteins, etc., addition of agents, reaction, and analysis are continuously performed while the sample solution flows through pipelines. By the automation, the analytical time can be further decreased and measurement errors can also be further decreased so that the measurement precision can be improved.

(C) In particular, the apparatus for analysis according to the present invention is suitable for the quantitation of very small amounts of proteins, etc., contained in strongly acidic solutions such as electrolytic solutions and plating solutions. Since proteins dissolved in strongly acidic solutions are likely to be decomposed and denatured, when the analytical time is increased, the measurement precision is decreased by a large degree. Conventional batch type analytical methods take about 24 hours of analytical time and the analytical error is so large that the process control cannot be performed in real time. On the other hand, according to the analytical system of the present invention, the analytical results can be promptly obtained in a short time after sampling which makes the analytical precision superior.

(d) In the analytical system of the present invention, since a hydrophobic adsorption resin is used as a device for separating proteins and conventional filters, etc., are not used, the analytical precision does not depend on filter pores. The aforementioned adsorption resin can be easily regenerated and can be repeatedly used so that the analytical cost can be decreased.

EXAMPLES

The present invention will be specifically explained below by using examples.

Example 1

A quantitative analysis of gelatins (glues) in a copper electrolytic solution containing 1.5 M of sulfuric acid, 40 g/L of copper, and 20 g/L of nickel was performed using the analytical system according to the present invention as shown in FIG. 1. A resin-filled column 21 for adsorbing proteins war made of a tube of 1 mm in diameter, 150 mm in length, and 0.11 mL in volume, filled with a hydrophobic nonpolar adsorbing resin SM-2 (trade name). 1 mL of sample solution was used. Dilute sulfuric acid having a concentration of 0.1 M was used as the carrier solution, and 40% acetonitrile aqueous solution was used as the eluant solution for proteins. The first stage GPC column 32 was filled with a hydrophilic polymer gel having an exclusion molecular weight limit of $2.0 \times 10^5$, and the second stage GPC column 32 was filled with the hydrophilic polymer gel having an exclusion molecular weight limit of $2.5 \times 10^6$. As the detecting device 35, an ultraviolet and visible spectrophotometer equipped with a flow cell having an optical path length of 20 mm was used with a measurement wavelength of 209 nm.

After the dilute sulfuric acid and water were passed through the resin-filled column 21 for washing, the sample solution was passed through the sample loop 10 so as to be held to a specified amount of 1 mL. Then dilute sulfuric acid as a carrier was introduced into the loop 10 so that the sample solution was fed to the aforementioned column 21 and gelatins in the sample solution were adsorbed on the resin. The solution that passed through the column 21 was discharged to the outside of the system. Next, the pipelines were switched so that the eluant solution was fed into the column 21, the gelatins adsorbed on the resin were eluted, and the resulting eluate solution was led to the mixing section 26 through the pipeline 24. Phosphoric acid having a concentration of 0.1 M was used as a buffer solution, and was mixed with the eluate solution passing through the pipeline 24. The resulting mixed solution was led to the two stages of GPC columns 32 so that the gelatins in the solution were fractionated and diffused. The resulting solution was led to the detecting devices 35 and the behaviors of the gelatins during decomposition were measured. The results thereof are shown in FIG. 3 and FIG. 4.

Figure 3:
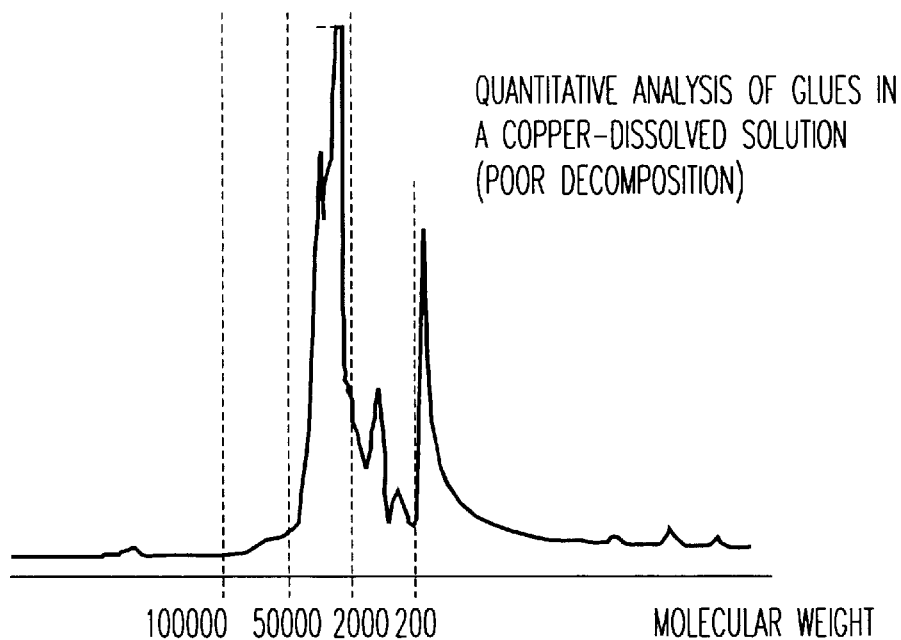
FIG. 3 is a graph showing analytical results according to Example 1.
Figure 4:
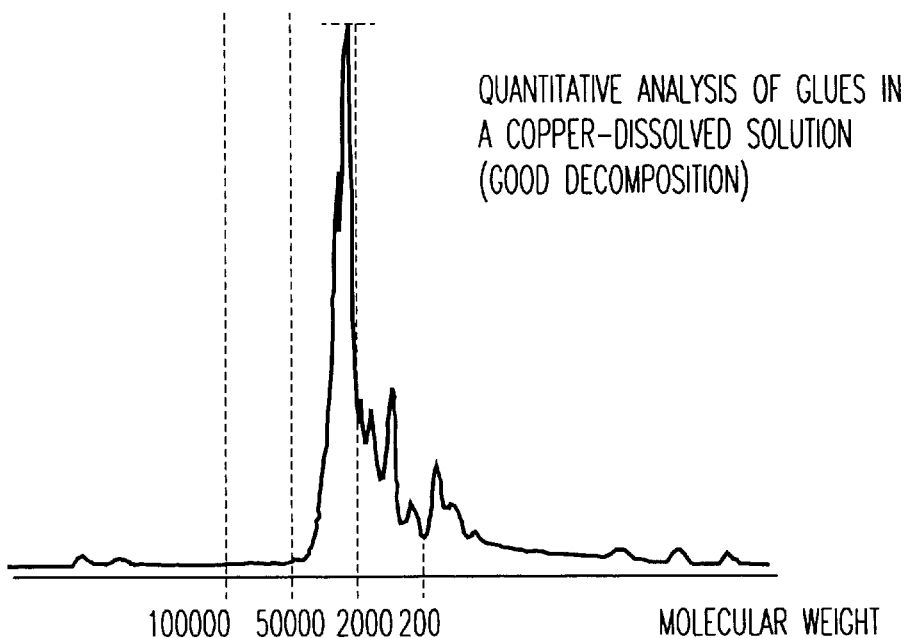
FIG. 4 is a graph showing analytical results according to Example 1.

As shown in FIG. 3, the gradual rise of the chromatogram curve at a molecular weight of about 100,000 to 50,000 in terms of polyethylene oxide, indicates a poor decomposition of gelatins. In addition, the presence of peaks at a molecular weight in the neighborhood of 200 indicates that intermediate products in this range are generated. On the other hand, as shown in FIG. 4, the sharp rise of the chromatogram curve at a molecular weight of about 100,000 to 50,000, and the absence of a large peak at a molecular weight in the neighborhood of 200, indicates a good decomposition of gelatins.

Example 2

Figure 5:
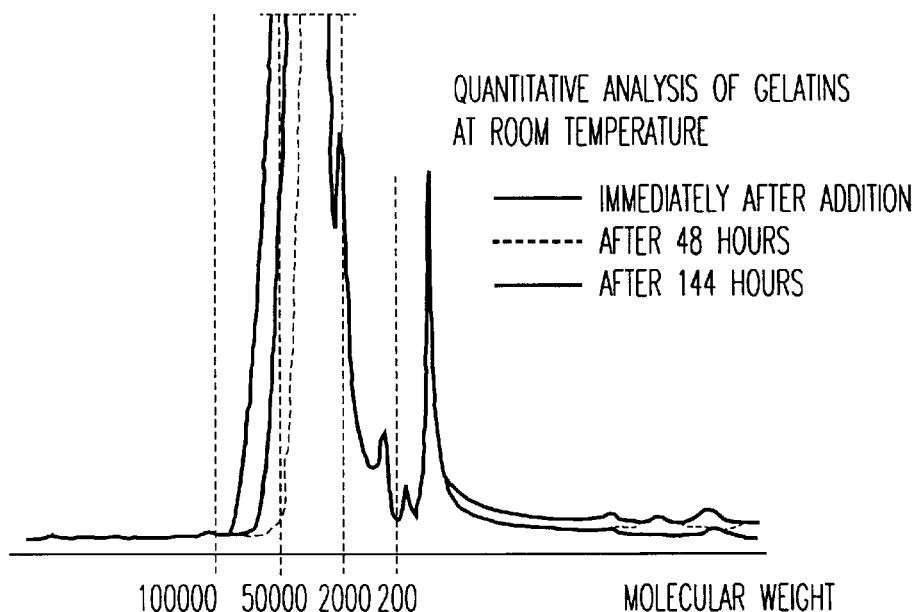
FIG. 5 is a graph showing analytical results according to Example 2.
Figure 6:
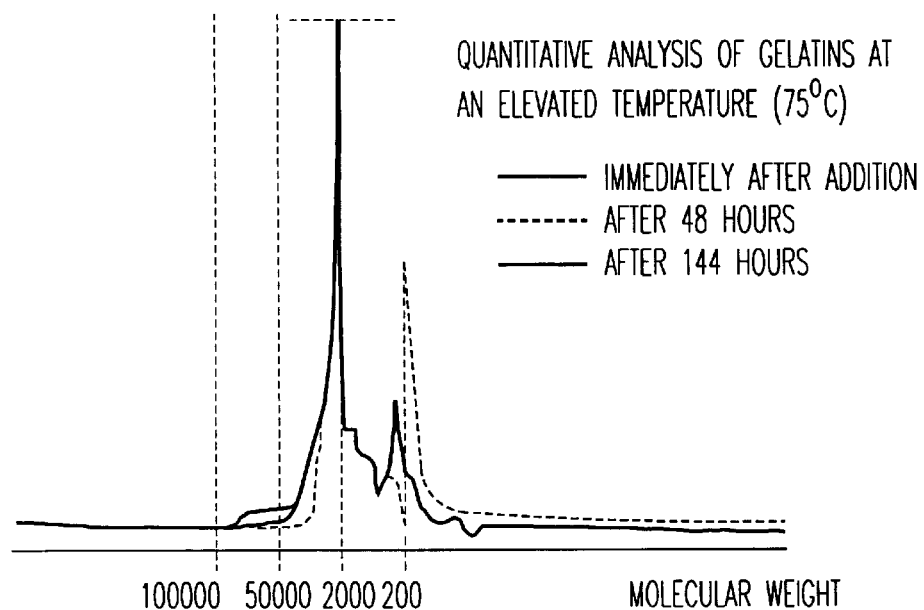
FIG. 6 is a graph showing analytical results according to Example 2.

Regarding the copper electrolytic solution similar to that in Example 1, behaviors of the gelatins during decomposition in different environments, that is, at room temperature and at an elevated temperature of 75° G, were measured in a manner similar to that in Example 1. The measurements were continuously performed from immediately after the addition until 144 hours after the addition and changes thereof with time were examined. The results thereof were shown in FIG. 5 and FIG. 6. As shown in the drawings, the chromatogram curve gradually shifts to the lower molecular weight side with the passage of measuring time. This indicates that the decomposition of gelatins proceeds with the passage of measuring time. As shown in FIG. 5, the decomposition speed of the gelatins at room temperature is lower than that of the gelatins at an elevated temperature, although the decomposition state of the gelatins after a lapse of 24 hours or more is very different from that of the gelatins immediately after the addition. On the other hand, as shown in FIG. 6, at an elevated temperature, the quantitative curve shifts by a large degree to the lower molecular weight side even after a lapse of 3 hours from the time of addition. Therefore, it is clear that a prompt analysis with minimal time is necessary for controlling the electrolytic solution.

Example 3

Figure 7:
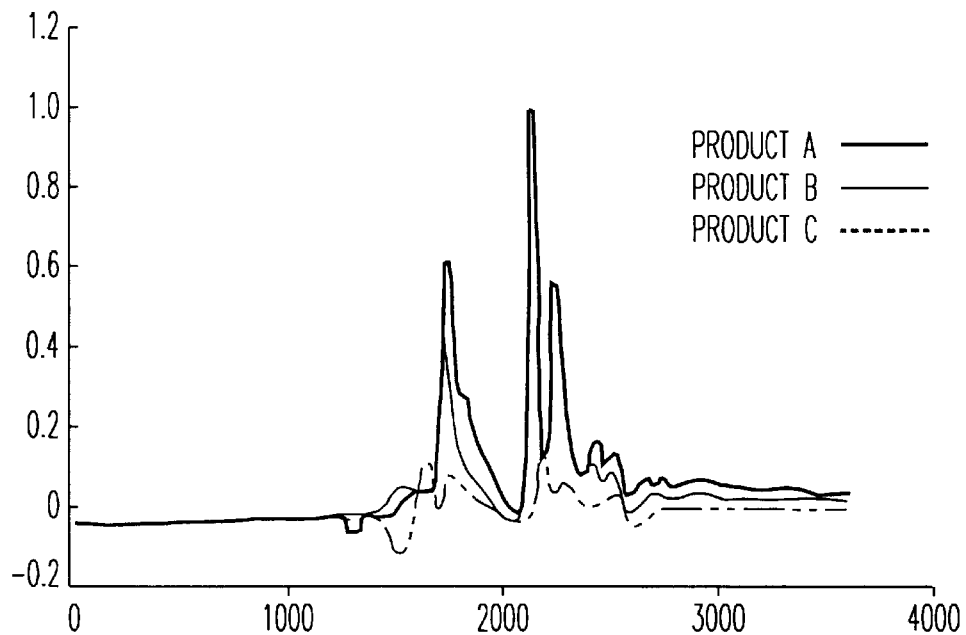
FIG. 7 is a graph showing analytical results according to Example 3.

A quantitative analysis of gelatins (glues) in a copper electrolytic solution containing 1 to 2 M of sulfuric acid, 30 to 45 g/L of copper, and 0 to 40 μL of nickel was performed using the apparatus for analysis according to the present invention as shown in FIG. 1. A resin-filled column for adsorbing proteins was made of a commercially available column housing filled with a hydrophobic nonpolar adsorbing resin SM-2 (trade name). 25 mL of a sample solution was used. Dilute sulfuric acid having a concentration of 20 mM was used as a carrier solution, and 0.1 M phosphoric acid buffer solution (20% acetonitrile) was used as an eluant solution for proteins. The first stage GPC column 32 was filled with a hydrophilic polymer gel having an exclusion molecular weight limit of $2.5 \times 10^6$, and the second stage GPC column 32 was filled with the hydrophilic polymer gel having an exclusion molecular weight limit of $2 \times 10^5$. As the detecting device 35, an ultraviolet and visible spectrophotometer equipped with a flow cell having an optical path length of 20 mm was used with a measurement wavelength of 209 nm. After dilute sulfuric acid was passed through the resin-filled column 21 for washing, the sample solution was passed through the sample loop 10 so as to be held to a specified amount of 5 mL. Then, dilute sulfuric acid as the carrier was introduced into the loop 10 so that the sample solution was fed to the aforementioned column 21 and gelatins (glues) in the sample solution were adsorbed on the resin. The aforementioned actions were repeated five times. The solution which passed through the column 21 was discharged to the outside of the system. Next, the pipelines were switched so that the eluant solution was fed into the column 21, the gelatins (glues) adsorbed on the resin were eluted, and the resulting eluate solution was led to a degasser 27 through the pipeline 24. The gaseous components in the eluate solution were degassed with the degasser 27, and the resulting solution was led to the two stages of GPC columns 32, provided in the thermostatic chamber 34 kept at 45° C., through the pipeline 28 so that the gelatins (glues) in the solution were fractionated and diffused. The resulting solution flowing out of the columns was led to the detecting devices 35 and the distribution of the molecular weights of the gelatins (glues) was measured. The results thereof are shown in FIG. 7. FIG. 7 shows distributions of the molecular weights in the electrolytic solutions when the gelatins (glues), manufactured by different manufacturers, were used in electrolytic smelting. As is confirmed from the drawing, the distribution states of the molecular weights were different depending on the manufacturer.

Example 4

Figure 8:
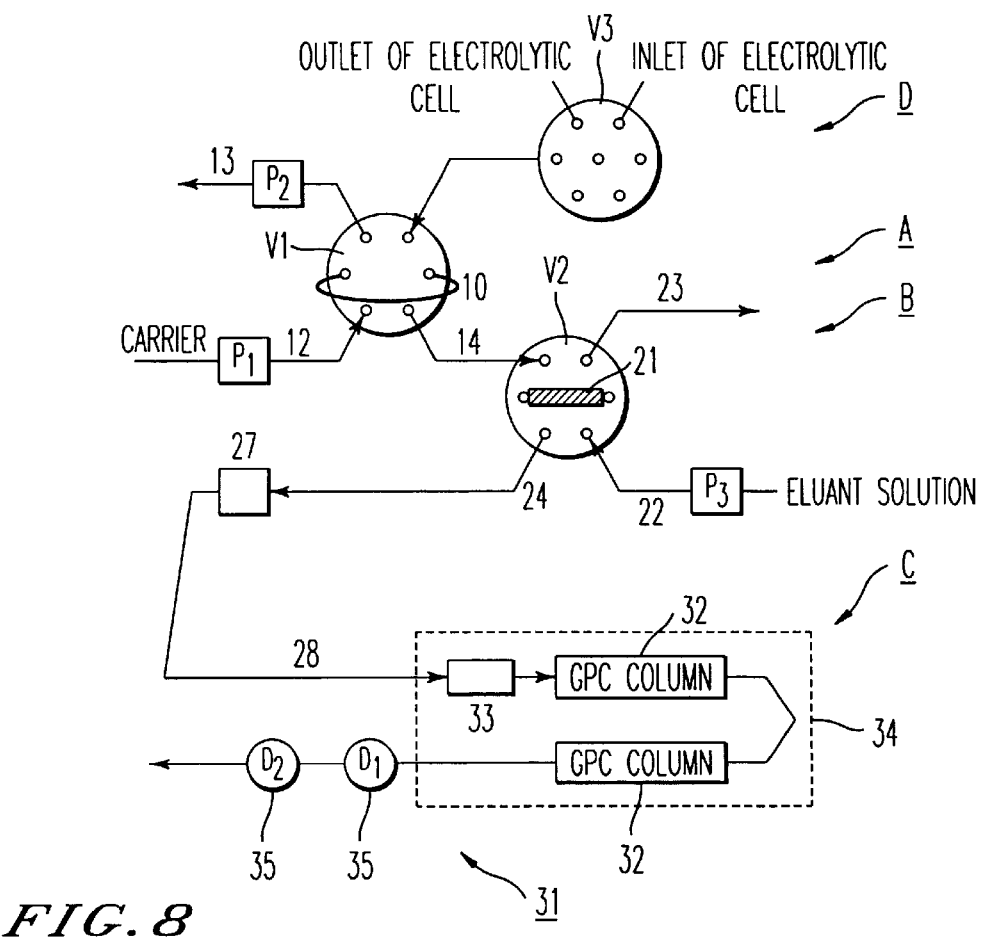
FIG. 8 is a conceptual diagram of an analysis apparatus (system) according to the present invention.
Figure 9:
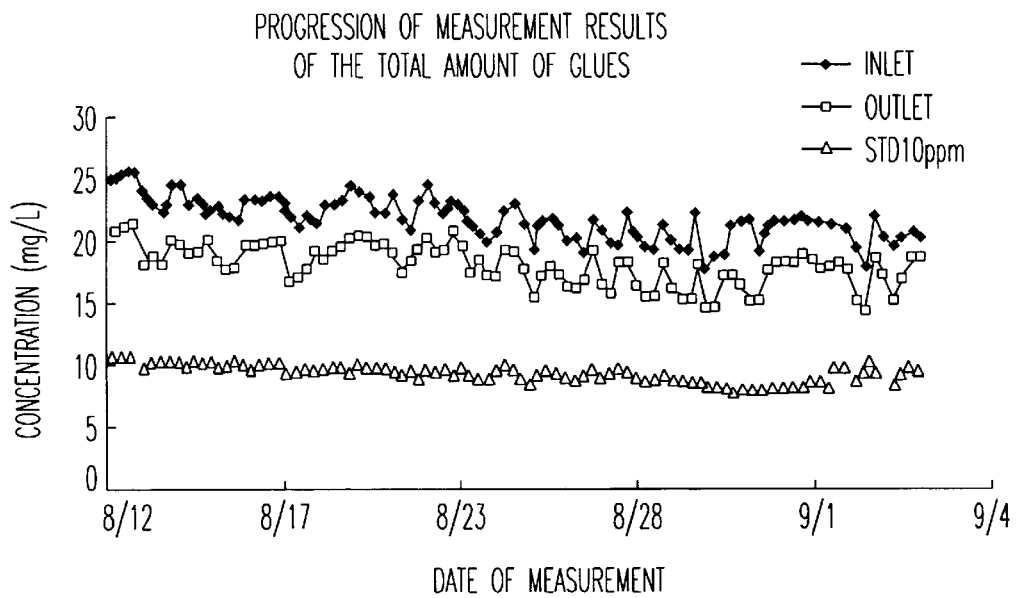
FIG. 9 is a graph showing analytical results according to Example 4.

The total concentration of the gelatins (glues) at the inlet and outlet of the electrolytic cell were treasured using the apparatus as shown in FIG. 8. In addition, the concentrations of the decomposition products having molecular weights in the neighborhood of 100, generated from decomposition of the gelatins during the electrolytic smelting, were measured. The apparatus as shown in FIG. 8 corresponds to the apparatus for analysis as shown in FIG. 1, further provided with a sample selecting section D, which could select an appropriate sample from a plurality of samples, in addition to the sample introduction section A. Furthermore, this sample selecting section D was provided with pipelines connected to the inlet and the outlet of the electrolytic cell, configured so as to take samples from each of the inlet and the outlet of the electrolytic cell by switching the pipelines connected to the sample selecting section D. This series of operations was automatically performed by each operational part being controlled with a computer. The total concentration of gelatins (glues) and the concentrations of the decomposition products in the electrolytic solutions, taken from the inlet and the outlet of the electrolytic cell, were measured four times per day using this apparatus for analysis. The aforementioned measurements were continuously performed for about one month, which is required for the formation of electrodeposited copper by electrolysis. Finally, the obtained progressions of the concentrations are shown in FIG. 9. The distributions of the molecular weights at the start and end of the analysis are shown in FIG. 10.

As shown in FIG. 9, the analytical values of the total concentration of gelatins (glues) are within the range of 20 to 25 ppm at the inlet side and are within the range of 15 to 22 ppm at the outlet side from the measurements. The concentrations at the inlet side have a tendency of being higher than the concentrations at the outlet side. Usually, in a step of electrolytic smelting, specified amounts, per hour, of gelatins (glues) are added at the inlet side of the electrolytic cell. As is confirmed from the results shown in FIG. 9, the gelatins are consumed in a step of electrolytic smelting.

Figure 10:
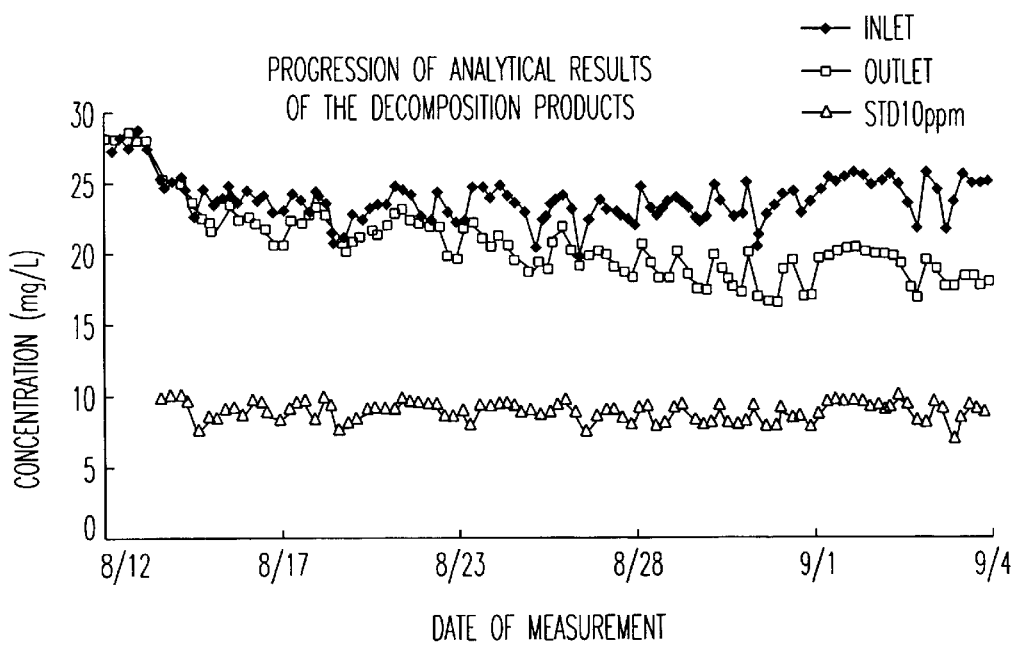
FIG. 10 is a graph showing analytical results according to Example 4.
Figure 11:
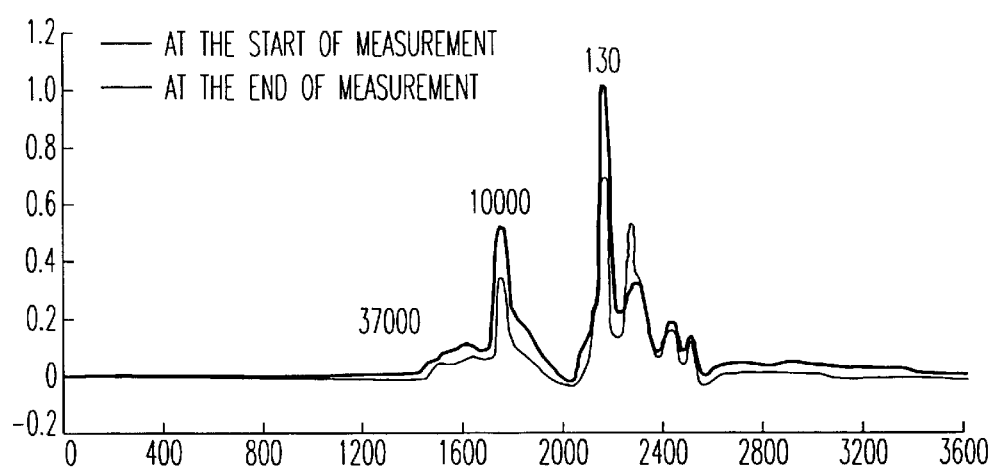
FIG. 11 is a graph showing analytical results according to Example 4.

As shown in FIG. 10, the concentrations of the decomposition products is nearly constant at the inlet side of the electrolytic cell from the measurements, although the concentrations at the outlet side have a tendency of being decreased with time. This is because decomposition products, having small molecular weights of less than about 100, were generated by the acceleration of the decomposition of the gelatins due to the generation of the electrodeposited copper, as is confirmed from the distributions of the molecular weights at the end of the measurement, indicating the presence of materials having peaks at the molecular weights of 100 or less, as shown in FIG. 11. Accordingly, the relationship between the total concentration of gelatins (glues) in the electrolytic solutions and the electrolytic smelting, and the relationship between the concentrations of the decomposition products in the electrolytic solutions and the electrolytic smelting, can be monitored online using the apparatus for analysis of the present invention. Therefore, the apparatus for analysis according to the present invention can be used for controlling operations.

While the present invention has been described with respect to specific embodiments, it is not confined to the specific details set forth, but includes various changes and modifications that may suggest themselves to those skilled in the art, all falling within the scope of the invention as defined by the following claims.

What is claimed is:

1. An organic macromolecular component analysis method comprising:
    providing a measurement system including a sample introduction section, a preparation section, and a measuring section;
    introducing a sample including an organic macromolecular component into the introduction section;
    transferring the sample to the preparation section;
    separating the organic macromolecular component from the sample; and
    moving the separated organic macromolecular component to the measuring section, wherein
        the separating comprises:
            adsorbing the organic macromolecular component on a resin in the preparation section;
            feeding an eluant solution into the preparation section; and
            eluting the organic macromolecular component adsorbed on the resin using the eluant solution;
            and further comprising
                introducing a mixture of the eluant solution and a phosphoric acid buffer solution into a detecting device in the measuring section wherein the phosphoric acid buffer solution is introduced into the detecting device at a flow rate of 1 mL/min or less.

2. The method according to claim 1, wherein
the introducing comprises:
    connecting the introduction section to a sample supply, and
    supplying the sample to the introduction section; and
the transferring comprises:
    disconnecting the introduction section from the sample supply,
    connecting a carrier solution supply to the introduction section,
    connecting the introduction section to the preparation section via a feed pipe,
    supplying a carrier solution from the carrier solution supply to the introduction section, and
    using the carrier solution to carry the sample from the introduction section through the feed pipe to the preparation section.

3. The method according to claim 2, wherein the carrier solution comprises at least one selected from the group consisting of sulfuric acid at a concentration of 0.1 M or less, hydrochloric acid at a concentration of 0.1 M or less, and nitric acid at a concentration of 0.1 M or less.

4. The method according to claim 1, wherein the eluant solution comprises a buffer solution for preventing the organic macromolecular component from coagulating.

5. The method according to claim 1, wherein the eluant solution comprises
20–40% of an alcohol selected from the group consisting of methanol, ethanol, propanol, butanol, pentanol, and hexanol; or
20–40% of acetonitrile.

6. The method according to claim 1, wherein the moving comprises adding to the separated organic macromolecular component a buffer solution for preventing the separated macromolecular component from coagulating.

7. The method according to claim 1, further comprising fractionating and analyzing the separated organic macromolecular component in the measuring section using gel permeation chromatography.

8. The method according to claim 1, further comprising fractionating and analyzing the separated organic macromolecular component in the measuring section to determine at least one of an amount of glue separated from the sample, an amount of gelatin separated from the sample, an amount of decomposition products of the glue, and an amount of decomposition products of the gelatin.

9. The method according to claim 1, wherein the resin comprises an acid-proof and hydrophobic adsorption resin.

10. The method according to claim 1, wherein the sample is selected from the group consisting of an electrolytic solution taken from a metallic electrolysis process and a plating solution taken from a plating process.

11. A method for controlling a metallic electrolysis process, the method comprising:
taking a sample solution from an electrolytic solution used in an metallic electrolysis process;
analyzing an organic macromolecular component in the sample solution using the method of claim 1;
measuring at least one of an amount of glue separated from the sample solution, an amount of gelatin separated from the sample solution, an amount of decomposition products of the glue, and an amount of decomposition products of the gelatin; and
feeding the results of the measurement back to the metallic electrolysis process.

12. A method for controlling a metallic electrolysis process, the method comprising:
taking a sample solution from a plating solution used in a plating process;
analyzing an organic macromolecular component in the sample solution using the method of claim 1;
measuring at least one of an amount of glue separated from the sample solution, an amount of gelatin separated from the sample solution, an amount of decomposition products of the glue, and an amount of decomposition products of the gelatin; and
feeding the results of the measurement back to the plating process.

13. An organic macromolecular component analysis method comprising the following steps:
providing a measurement system including a sample introduction section, a preparation section, and a measuring section;
introducing a sample including an organic macromolecular component into the introduction section;
transferring the sample to the preparation section;
a step for separating the organic macromolecular component from the sample; and
moving the separated organic macromolecular component to the measuring section, wherein the step for separating comprises the following steps:
a step for adsorbing the organic macromolecular component on a resin in the preparation section;
a step for feeding an eluant solution into the preparation section; and
a step for eluting the organic macromolecular component adsorbed on the resin using the eluant solution; and further comprising
introducing a mixture of the eluant solution and a phosphoric acid buffer solution into a detecting device in the measuring section wherein the phosphoric acid buffer solution is introduced into the detecting device at a flow rate of 1 mL/min or less.

14. An apparatus for flow analysis of an organic macromolecular component in a sample, the apparatus comprising a sample introduction section, a preparation section, and a measuring section, wherein
the introduction section is connected to the preparation section;
the preparation section is connected to the measuring section;
the preparation section comprises a separation device to separate the organic macromolecular component from the sample; and
the measuring section comprises an measurement device to fractionate and analyze the separated organic macromolecular component and a detecting device; wherein a mixture of an eluant solution and a phosphoric acid buffer solution is introduced into the detecting device of the measuring section wherein the phosphoric acid buffer solution is introduced into the detecting device at a flow rate of 1 mL/min or less.

15. The apparatus according to claim 14, wherein
the separation device comprises a column including a resin for adsorbing the organic macromolecular component in the sample; and
the apparatus further comprises:
a sample feed pipe from the introduction section to the preparation section;
an eluant pipe from an eluant supply to the preparation section; and
a valve to create a fluid connection between the column and either the sample feed pipe or the eluant pipe.

16. The apparatus according to claim 15, wherein the resin comprises an acid-proof and hydrophobic adsorption resin.

17. The apparatus according to claim 15, wherein the sample feed pipe and the eluant pipe have internal diameters of 1 mm or less.

18. The apparatus according to claim 14, further comprising a buffering section, between the preparation section and the measuring section, for adding a buffer solution to the organic macromolecular component to prevent the organic macromolecular component from coagulating.

19. The apparatus according to claim 14, wherein the measurement device comprises a gel permeation chromatograph.

20. The apparatus according to claim 19, wherein the gel permeation chromatograph comprises a column including with a hydrophilic polymer gel having an exclusion molecular weight limit of $5 \times 10^3$ or more.

21. The apparatus according to claim 20, wherein the column comprises a plurality of column stages; and each of the plurality of column stages includes a different hydro philic polymer gel having a different exclusion molecular weight limit.

22. The apparatus according to claim 14, wherein the measuring section comprises a thermostatic chamber; and the thermostatic chamber comprises a gel permeation chromatograph.

23. The apparatus according to claim 14, further comprising
an automatic device for controlling at least one of:
a flow of the sample in the sample introduction section,
a flow of the sample in the preparation section,
a temperature in the measuring section, and
a detector in the measuring section.

24. An apparatus for flow analysis of an organic macromolecular component in a sample, the apparatus comprising a sample introduction section, a preparation section, and a measuring section, wherein the introduction section is connected to the preparation section;
the preparation section is connected to the measuring section;
the preparation section comprises a means for separating the organic macromolecular component from the sample; and
the measuring section comprises a means for fractionating and analyzing the separated organic macromolecular component and a detecting device; wherein a mixture of an eluant solution and a phosphoric acid buffer solution is introduced into the detecting device of the measuring section wherein the phosphoric acid buffer solution is introduced into the detecting device at a flow rate of 1 mL/min or less.

* * * * *

UNITED STATES PATENT AND TRADEMARK OFFICE
CERTIFICATE OF CORRECTION

PATENT NO. : 6,668,624 B2
DATED : December 30, 2003
INVENTOR(S) : Tani et al.

It is certified that error appears in the above-identified patent and that said Letters Patent is hereby corrected as shown below:

<u>Title page, Item [54] and Column 1, lines 1-4,</u>
Title, should read -- METHOD AND APPARATUS FOR ANALYZING ORGANIC MACROMOLECULAR COMPONENTS AND APPLICATION THEREOF --

Signed and Sealed this

Sixth Day of April, 2004

JON W. DUDAS
*Acting Director of the United States Patent and Trademark Office*